US011337921B2

(12) United States Patent
Moreau et al.

(10) Patent No.: US 11,337,921 B2
(45) Date of Patent: May 24, 2022

(54) MULTI-USE TORASEMIDE COMPOSITION

(71) Applicant: VETOQUINOL SA, Magny-Vernois (FR)

(72) Inventors: Marinette Moreau, Saint-Germain (FR); Elodie Lego, Lure (FR)

(73) Assignee: VETOQUINOL SA, Lure (FR)

(*) Notice: Subject to any disclaimer, the term of this patent is extended or adjusted under 35 U.S.C. 154(b) by 0 days.

(21) Appl. No.: 16/969,848

(22) PCT Filed: Feb. 15, 2019

(86) PCT No.: PCT/FR2019/050345
§ 371 (c)(1),
(2) Date: Aug. 13, 2020

(87) PCT Pub. No.: WO2019/158873
PCT Pub. Date: Aug. 22, 2019

(65) Prior Publication Data
US 2020/0375898 A1    Dec. 3, 2020

(30) Foreign Application Priority Data

Feb. 16, 2018  (FR) .......................................... 185135

(51) Int. Cl.
*A61K 31/44*   (2006.01)
*A61K 9/08*    (2006.01)
*A61K 47/10*   (2017.01)

(52) U.S. Cl.
CPC ................ *A61K 9/08* (2013.01); *A61K 31/44* (2013.01); *A61K 47/10* (2013.01)

(58) Field of Classification Search
CPC ..................................................... A61K 31/44
See application file for complete search history.

(56) References Cited

U.S. PATENT DOCUMENTS

| 4,861,786 A | 8/1989 | Demmer et al. |
| 2015/0148335 A1* | 5/2015 | Bova .......................... A61P 9/00 514/212.07 |
| 2017/0000814 A1 | 1/2017 | Mahoney et al. |

OTHER PUBLICATIONS

International Search Report dated Apr. 23, 2019 (five pages including English translation) from corresponding PCT Application No. PCT/FR2019/050345.
Written Opinion dated Apr. 23, 2019 (five pages—French language) from corresponding PCT Application No. PCT/FR2019/050345.
International Preliminary Report on Patentability dated Aug. 18, 2020 (six pages—French language) from corresponding PCT Application No. PCT/FR2019/050345.
Article, Peddle et al., "Effect of torsemide and furosemide on clinical, laboratory, radiographic and quality of life variables in dogs with heart failure secondary to mitral valve disease", Journal of Veterinary Cardiology (2012) 14, 253-259, doi: 10.1016/j.jvc.2012.01.003.

* cited by examiner

*Primary Examiner* — Benjamin J Packard
(74) *Attorney, Agent, or Firm* — Crowell & Moring LLP; John C. Freeman, Esq.

(57) ABSTRACT

An aqueous composition including torasemide and at least one organic solvent, to a bottle or container including the composition, and to a kit including the bottle or container and a device for delivery of the composition (for example a syringe).
A use of at least one organic solvent for increasing the stability and/or the antimicrobial properties of a composition including torasemide.
A method for preparing the composition.

39 Claims, 2 Drawing Sheets

MULTI-USE TORASEMIDE COMPOSITION

This application is a National Stage application of International Application No. PCT/FR2019/050345, filed Feb. 15, 2019, wherein the above-mentioned International Application claims the benefit under 35 U.S.C. § 119(a) of the filing date of Feb. 16, 2018 of French Patent Application No. 1851353, the entire contents of each of which are incorporated herein by reference.

BACKGROUND OF THE INVENTION

Technical Field

The present invention relates to an aqueous composition including torasemide and at least one organic solvent, to a bottle or container including the composition and to a kit including the bottle or container and a system for administering the composition (for example a syringe).

The present invention also s to a use of at least one organic solvent for increasing the stability and/or the antimicrobial properties of a composition including torasemide.

Finally, the present invention also relates to a method for preparing a composition according to the invention.

PRIOR ART

Torasemide or torsemide (1-isopropyl-3-[(4-m-toluidino-3-pyridyl)sulfonyl]urea) is a known active ingredient, which possesses strong diuretic action. It is used in the treatment of edemas associated with heart failure, kidney diseases and in the treatment of hypertension, in human and veterinary therapeutics.

Torasemide ($C_{16}H_{20}N_4S$, M=348.4 g·mol$^{-1}$, CAS: 56211-40-6) has the following structural formula I:

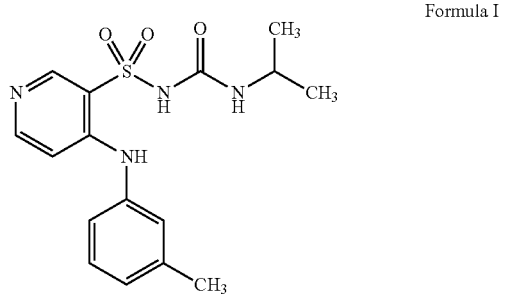 [SMILES: Cc1cccc(Nc2ccncc2S(=O)(=O)NC(=O)NC(C)C)c1]

Formula I

It is marketed notably under the trademarks Demadex®, Diuver®, Dytor®, Examide® and Upcard®.

The diseases for which treatment including torasemide is recommended are chronic diseases that generally require daily treatment.

Recent studies presented in Peddle et al. (J. Vet. Cardiolog 2012) have recommended favoring torasemide for a better diuretic effect. Thus, there is growing interest in torasemide for treating heart disorders in particular. Despite these encouraging results, torasemide has a small (or narrow) therapeutic margin, meaning that any variation of its concentration in the organism, even slight or moderate, may possibly lead to undesirable, potentially serious effects. It is therefore important to be able to distribute the required dose.

An ion imbalance in humans or animals being treated is observed in chronic treatment. This imbalance leads to other undesirable effects such as a drop in pressure or increase of aldosterone and creatinine.

To date, furosemide (CAS: 54-31-9) constitutes the reference treatment. It is generally administered by the oral or intravenous route. Recently, scored tablets based on torasemide have been marketed in response to the problem of a narrow therapeutic margin and adjustment of the dose as a function of the weight of the person or animal.

However, this solution does not allow adjustment of the dose taking into account the entire range of available weights.

Moreover, the solubility of torasemide depends on the pH of the solution. The stability of torasemide in solution is, moreover, a function of the additives and excipients used in the composition. Thus, torasemide is insoluble at a pH between about 2 and 7 (FIG. 1).

Thus, torasemide is known to have low stability in an aqueous medium. Single-use injectable alkaline solutions based on torasemide are known in the prior art. U.S. Pat. No. 4,861,786 in particular describes an injectable alkaline torasemide composition including a physiologically compatible buffer with a pH between 9.3 and 9.9 and from 5 to 20% of an organic solvent, the organic solvent being selected from the group including polyethylene glycols (having a molecular weight between 100 and 1500 g·mol$^{-1}$), polypropylene glycols (having a molecular weight between 50 and 1000 g·mol$^{-1}$), glycerol, propylene glycol, ethanol and propanol. These compositions include from 2 to 40 mg·ml$^{-1}$ of torasemide. For reasons of stability, and in particular the appearance of crystals, the pH must be between 9.3 and 9.9, and the percentage of solvents must be below 20%.

Thus, the injectable alkaline torasemide compositions of the prior art have neither sufficient stability, nor an antimicrobial effect guaranteeing good preservation. Furthermore, their properties do not allow multiple usage (or multi-use), that is, repeated use of the same composition over a period of time ranging from several hours to several days.

The known compositions also do not offer a composition which in addition to increased stability and an antimicrobial effect, offers greater freedom for modulating the doses at the time of administration.

There is therefore a real need for a multi-use aqueous composition, which may be administered by the oral route or the parenteral route, and that overcomes these faults, drawbacks and obstacles of the prior art. There is also a need for a bottle or container including such compositions allowing extremely precise control of dosage in humans or animals, reduction of costs and thus overall improvement of the treatment.

DISCLOSURE OF THE INVENTION

The applicant has developed torasemide compositions including at least one organic solvent at a percentage by weight greater than or equal to 30%. Not only is the physical, chemical and/or antimicrobial stability of the composition improved, but it is so over wider ranges of pH, namely between 7.5 and 10, preferably between 8 and 9.9 and even more preferably between 9 and 9.9. Thus, the compositions according to the present invention are stable for a time of at least 24 months, preferably 36 months at a storage temperature between 25 and 30° C. The improvement of these properties makes the composition suitable for multiple usage (or multi-use), namely repeated use of the same composition over a period of time ranging from several hours to several days.

Furthermore, the compositions according to the invention have an antimicrobial preservation efficacy that complies with the American and European pharmacopeias.

Thus, not only is the stability improved, but it is so over an extended range of pH and in addition the composition has the benefit of an antimicrobial effect. The latter makes it possible for example to save on an antimicrobial preservative in the torasemide composition.

The present invention thus relates to an aqueous composition including torasemide and at least one organic solvent, wherein the concentration of organic solvent by weight may be greater than or equal to 30% relative to the total weight of the composition, preferably greater than or equal to 35% and even more preferably greater than or equal to 40%. Preferably, the concentration of organic solvent may be less than or equal to 70%.

"Aqueous composition" means a composition including water. In the context of the present invention, an aqueous composition includes at least water, an organic solvent and torasemide.

Advantageously, the concentration of torasemide by weight may be between 0.01% and 5% relative to the total weight of the composition, preferably between 0.1 and 3% and even more preferably between 0.1 and 2%. The concentration of torasemide by weight expressed in $mg \cdot ml^{-1}$ may be between 0.1 and 50 $mg \cdot ml^{-1}$, preferably between 1 and 30 $mg \cdot ml^{-1}$ and even more preferably between 1 and 20 $mg \cdot ml^{-1}$. The concentration of torasemide by weight may be for example 1, 2, 3, 4, 5, 6, 7, 8, 10, 12, 15 or 20 $mg \cdot ml^{-1}$. Advantageously, the compositions according to the invention are free from impurities. In the context of the invention, "impurities" means particles resulting from degradation of torasemide, or from precipitation of torasemide in the form of crystals, of molecules of the aldehyde or ketone type. Preferably, the total concentration of unknown or known impurities, such as impurities A and B (European Pharmacopeia) or impurities A and E (according to the USP) may be below 5%. The compositions according to the invention may be in the form of clear solutions. In the context of the invention, "clear" means a solution that does not comprise visible particles according to the monograph of the European Pharmacopeia.

Advantageously, the at least one organic solvent may be selected from the group including alcohols derived from propane. For example, the organic solvent may be selected from the group including propylene glycol (also called propane-1,2-diol or PG), glycerol (also called 1,2,3-propanetriol), propane-1,3-diol (also called PDO), propanol (also called propan-1-ol), isopropanol (also called propan-2-ol) and mixtures thereof. Preferably, the organic solvent may be selected from the group including glycerol and propylene glycol.

Advantageously, the compositions according to the present invention may further include a physiologically compatible buffer or an alkalizing agent. The buffer or alkalizing agent may be selected for example from the group including tromethamine (TRIS), triethanolamine, diethanolamine, monoethanolamine, sodium hydroxide, potassium hydroxide, ammonium hydroxide and meglumine. The concentration of buffer or alkalizing agent by weight may be between 1 and 5% relative to the total weight of the composition, preferably between 1 and 2%.

Advantageously, the composition according to the present invention may further include a rheology modifier (or thickener). The rheology modifier may be for example a hydrophilic synthetic polymer of acrylic acid (carbomer), a polysaccharide (cellulose derivatives, chitosans, starches or alginates), a gum, polyvinyl povidone, a poloxamer (Pluronic), hydrophilic silica, or a poly(meth)acrylate. The carbomer may be selected from the group including the homopolymer of 2-propenoic acid such as for example Carbopol 971NF, 974, 934P or 941. The polysaccharide may be selected from the group including starch and derivatives thereof, cellulose derivatives such as for example hydroxy ethylcellulose (HEC), ethylcellulose (EC), carboxymethylcellulose (CMC) and hydroxypropyl cellulose (HPC), derivatives of chitosan such as for example deacetylated chitin, copolymers of glucosamine and N-acetylglucosamine with different degrees of acetylation and having a molecular weight from 10 000 to 1 000 000. The gums may be selected from the group including xanthan gum and guar gum (galactomannan). "Derivative" means a conjugated base, a salt, ether, ester or, more generally, a compound that is derived from a similar compound by a chemical reaction. The concentration of rheology modifier by weight may be between 0.01 and 10% relative to the total weight of the composition, preferably between 0.1 and 5% and even more preferably between 0.1 and 2%.

Advantageously, the viscosity of the compositions according to the present invention may be between 0.001 and 5 Pa·s. The viscosity makes it possible to obtain optimal distribution of the active ingredient at the time of administration of the composition.

Advantageously, the composition according to the present invention may further include an agent for adjusting the osmolarity of the composition. The agent may be selected for example from sugar (glucoses), NaCl or KCl.

Advantageously, the composition according to the present invention may further include a sweetener. The sweetener may be selected from the group including saccharin (saccharin sodium), potassium acesulfame, advantame, aspartame, erythritol and isomalt. The concentration of sweetener by weight may be between 0.01 and 2% relative to the total weight of the composition. "Sweetener" or "sweetening agent" means, in the sense of the present invention, a compound or mixture of compounds having a sweet taste. Addition of this type of compound to the composition increases the palatability of the latter, when it is intended to be administered by the oral route, and thus makes it more easily accepted b the subject, especially when the drug is intended for an animal.

Advantageously, the composition according to the present invention may further include any pharmaceutically acceptable excipient. The composition may thus include one or more surfactant(s), inorganic compound(s) or isotonic agent(s).

Advantageously, the compositions according to the invention may have a pH between 7.5 and 10, preferably between 8.0 and 9.9 and even more preferably between 9 and 9.9 or else 9.3 and 9.9. The pH of the compositions may easily be adapted by a person skilled in the art as a function of the solubility and the amount of components in the composition, and in particular as a function of the solubility and the amount of torasemide. The pH of the compositions according to the invention may be adjusted by means of any pharmaceutically acceptable acid or base. The pH may for example be adjusted by means of NaOH, HCl, meglumine (N-methylglucamine), or tromethamine.

The improved stability of the compositions according to the invention also has the advantage of allowing greater modulation of the treatments, by reducing the constraints usually associated with torasemide. The compositions according to the invention supply a solution that is more adapted to each patient, notably owing to the possibility of more easily adjusting the dose distributed to all the potential body masses. For the first time in treatments based on torasemide, a composition addresses the problem of adjustment of dose to weight, for this substance, which has a narrow therapeutic margin.

Also for the first time, a torasemide composition is suitable for multiple use (or multi-use) and does away with the constraints associated with single-use compositions. This is reflected for example in a decrease of the amount of packaging, more flexible constraints on usage or ease of storage of a composition that has already been opened, which would be intended to be reused.

The compositions according to the invention are thus suitable both for chronic treatment (for example in the form of an oral composition) and for emergency treatment (for example in the form of an injectable composition). The volume of liquid administered to the person or to the animal may be adjusted as a function of the therapeutic dose required and the subject's body weight.

Advantageously, the compositions according to the invention may be administered by the oral, subcutaneous (SC), intramuscular (IM) or intravenous (IV) route.

According to another aspect, the invention relates to a composition according to the invention for use as a drug, in particular in the treatment of the clinical signs, including edema and fluid collection, associated with congestive heart failure, and treatment of kidney diseases and hypertension.

The invention thus also relates to:
- the use of a composition according to the invention for treating the clinical signs, including edema and fluid collection, associated with congestive heart failure, and for treating kidney diseases and hypertension,
- a method for treating the clinical signs, including edema and fluid collection, associated with congestive heart failure, method for treating kidney diseases and hypertension, comprising administration of a composition according to the invention.

The present invention also relates to the use of at least one organic solvent, at a concentration by weight greater than or equal to 30%, preferably greater than or equal to 35% and even more preferably greater than or equal to 40%, in an aqueous composition comprising torasemide. Preferably, the concentration by weight of at least one organic solvent may be less than or equal to 70%. The present invention also includes the use of at least one organic solvent, at a concentration by weight greater than or equal to 30%, preferably greater than or equal to 35% and even more preferably greater than or equal to 40% for increasing the stability of an aqueous composition including torasemide and/or imparting antimicrobial properties to the composition; that is, the composition is stable for a period of at least 24 months, preferably 36 months, at a temperature between 25° C. and 40° C., preferably 30° C. For example, the composition is stable for at least 24 months at a temperature of 30° C. or at least 36 months at a temperature of 25° C. Furthermore, the composition may, after opening, owing to its physical, chemical and microbiological stability, be stored for up to 28 days.

The invention also relates to a method for preparing the compositions according to the invention comprising the steps:
(a) adding the buffer or the alkalizing agent to water at room temperature and stirring to obtain mixture 1,
(b) adding torasemide to mixture 1 and stirring to obtain mixture 2,
(c) gradually adding the rheology modifier with stirring to obtain mixture 3,
(d) optionally adding one or more pharmaceutically acceptable excipient(s) and stirring until a clear solution is obtained (mixture 4),
(e) adding at least one organic solvent and stirring until a clear solution is obtained (mixture 5),
(f) optionally adjusting the volume while stirring,
(g) optionally adjusting the pH, and obtaining the composition according to the invention. Stirring may be mechanical (magnetic stirrer) and/or carried out using a turbine.

According to another aspect, the present invention also relates to a bottle or container including a composition according to the present invention.

Advantageously, the bottle may be provided with a cap, a reducer or any other opening system facilitating delivery of the composition. The device, which houses a syringe or other system for administering the composition makes it possible, as a function of the graduation, to administer just the dose that is required, effective and adapted to each treatment. The device makes it possible to limit microbial contamination during use of the composition according to the present invention, as the system for administration (i.e. the syringe) does not come into contact with the composition. For example, during accidental contact, the antimicrobial properties of the composition protect it from possible contamination.

Finally, the present invention also relates to a kit including:
- a bottle or container including a composition according to the present invention; and
- a system for administering the composition.

"System for administering the composition" means any system for taking the composition from the bottle or container and then administering it by the oral, SC, IM or IV route, such as for example a dropper, a dosing cap or a syringe. Other advantages will become apparent to a person skilled in the art on reading the examples given hereunder.

BRIEF DESCRIPTION OF THE FIGS.

EXAMPLES

Example 1

Figure 1:
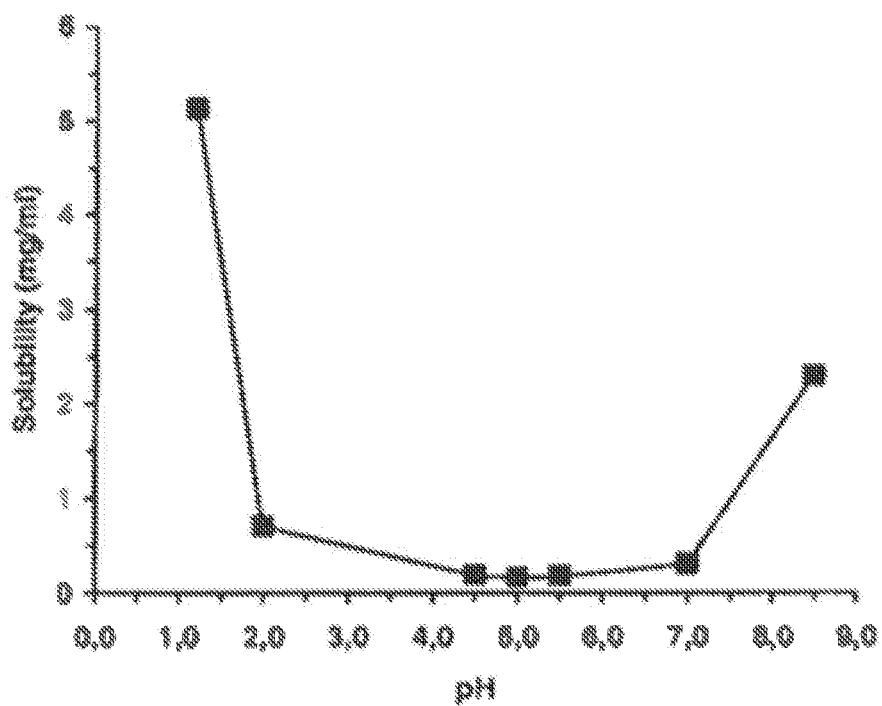
FIG. 1 shows a solubility curve of torasemide (in mg·ml$^{-1}$) as a function of pH.
Figure 2:
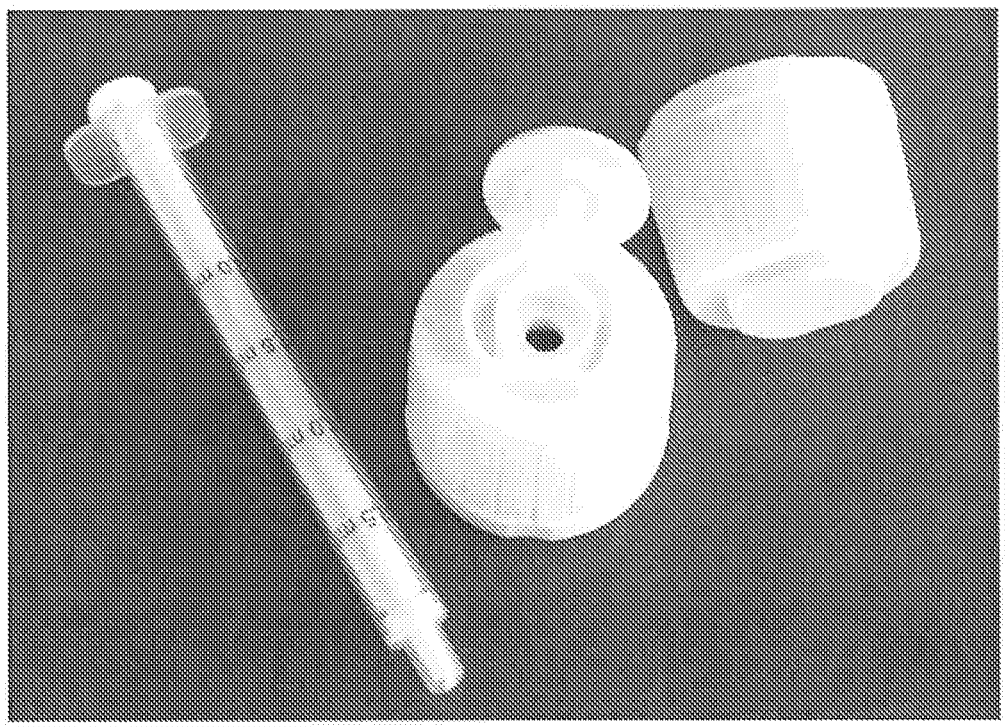
FIG. 2 shows a cap and a system from administering the composition (syringe).
Figure 3:
FIG. 3 shows two examples of kits according to the present invention (left and right) including a bottle provided with a cap and a system for administration (syringe) of the composition and a reducer (center).

Preparation of a Composition According to the Invention

Preparation of a Mixture 1:
Water and tromethamine (buffer) are introduced at room temperature (18-25° C.) with stirring by means of a deflocculating turbine (speed: 200-600 rpm, duration: about 15 min).

Preparation of a mixture 2:
Torasemide is added to mixture 1, with stirring by means of a deflocculating turbine (speed: 200-600 rpm, duration: about 15 min).

Preparation of a mixture 3:

The polymer is added gradually to mixture 2, with stirring by means of a deflocculating turbine and mechanical stirring (speed: 200-600 rpm, duration: about 15 min).

Preparation of a mixture 4:

The remaining excipients (apart from the organic solvent) are added to mixture 3, maintaining stirring until a clear solution is obtained.

Preparation of a mixture 5:

Then the organic solvent (propylene glycol) is added to mixture 4, maintaining stirring until a clear solution is obtained.

Optionally, the volume is adjusted with water, with magnetic stirring, for a minimum time of 15 min.

Optionally, the pH is adjusted to the desired value.

The composition is obtained in the form of a colorless liquid of low viscosity.

The compositions in Table 1 below are prepared according to the above protocol, with the amounts indicated in the table.

TABLE 1 compositions, comparative example and according to the invention.

| Composition No. | Comparative 1 | Composition 1 | Composition 2 |
|---|---|---|---|
| Torasemide | 0.30% | 0.20% | 0.20% |
| Tromethamine (TRIS) | | 1.50% | 1.50% |
| Meglumine | 1.00% | | |
| PEG 400 | 10.00% | | |
| Propylene glycol | | 40.00% | 40.00% |
| Carbopol 971P | | 0.20% | |
| Natrosol 250G Pharm | | | 1.00% |
| Saccharin sodium | | 0.20% | |
| Hydrochloric acid | Q.S. pH 8.0-10 | Q.S. pH 9.3-9.7 | Q.S. pH 9.3-9.7 |
| WFI | Q.S. 100% | Q.S. 100% | Q.S. 100% |

Q.S. = quantity sufficient for. WFI = water for injection.

Example 2

Optimized Stability of the Compositions According to the Invention

The stability of compositions 1 and 2 was evaluated in accelerated harsh storage conditions: at a temperature of 40° C., at a relative humidity of 75% and for a time T=2 months.

For each of the compositions tested, the level of impurities is measured by the method corresponding to the active ingredient, described in the monographs of the European or American Pharmacopeia.

The results are presented in Table 2 below:

TABLE 2 stability tests of compositions 1 and 2.

| Composition No. | Comparative 1 | Composition 1 | Composition 2 |
|---|---|---|---|
| Macroscopic appearance | turbid | clear | clear |
| Torasemide content (per dose, 95-105%) | 100.30 | 99.10 | 100.00 |
| Each unknown impurity (≤0.3%) | 0.31 | 0.02 | 0.01 |
| Total unknown impurities (≤1.0%) | 0.41 | 0.07 | 0.04 |

"Unknown impurity" means the impurities, degradation products and chemical impurities classified as "B" and "A" in the European Pharmacopeia and "A" and "E" in the American Pharmacopeia (USP). The results obtained demonstrate that the compositions according to the invention are more stable than the compositions of the prior art. The compositions according to the invention thus meet the criteria required by the American and European pharmacopeias in terms of stability.

Example 3

Antimicrobial Properties of the Compositions According to the Invention

Antimicrobial efficacy was evaluated according to the European monograph.

The following compositions (A to I according to the invention and CE1 to CE7 counter-examples) were prepared according to the procedure of example 1.

TABLE 3

Efficacy of antimicrobial storage of different batches with 0.2% of carbomer and with different amounts of propylene glycol.

| | Percentage composition (in % w/w) | | |
|---|---|---|---|
| Ingredients | CE1 (0% PG) | CE2 (20% PG) | A (40% PG) |
| Torasemide | 0.20 | 0.20 | 0.20 |
| Tromethamine | 1.50 | 1.50 | 1.50 |
| Carbomer | 0.20 | 0.20 | 0.20 |
| Propylene glycol | 0.00 | 20.00 | 40.00 |
| Purified water q.s. w/w | 98.10 | 78.10 | 58.10 |
| Total (% w/w) | 100.00 | 100.00 | 100.00 |
| Efficacy of antimicrobial storage (Ph Eur) | NC | NC | C |
| S. aureus | C | C | C |
| E. coli | C | C | C |
| Ps. aeruginosa | C | C | C |
| C. albicans | C | C | C |
| A. brasiliensis | NC | NC | C |

NC = not compliant, C = compliant.

TABLE 4

Efficacy of antimicrobial storage of different batches with 1% of HEC and with different amounts of propylene glycol.

| | Percentage composition (in % w/w) | | |
|---|---|---|---|
| Ingredients | CE3 (0% PG) | CE4 (20% PG) | B (40% PG) |
| Torasemide | 0.20 | 0.20 | 0.20 |
| Tromethamine | 1.50 | 1.50 | 1.50 |
| Hydroxyethylcellulose | 1.00 | 1.00 | 1.00 |
| Propylene glycol | 0.00 | 20.00 | 40.00 |
| Purified water q.s. w/w | 97.30 | 77.30 | 57.30 |
| Total (% w/w) | 100.00 | 100.00 | 100.00 |
| Efficacy of antimicrobial storage (Ph Eur) | NC | NC | C |
| S. aureus | NC | C | C |
| E. coli | C | C | C |

TABLE 4-continued

Efficacy of antimicrobial storage of different batches with 1% of HEC and with different amounts of propylene glycol.

| | Percentage composition (in % w/w) | | |
|---|---|---|---|
| Ingredients | CE3 (0% PG) | CE4 (20% PG) | B (40% PG) |
| Ps. aeruginosa | C | NC | C |
| C. albicans | NC | C | C |
| A. brasiliensis | NC | NC | C |

NC = not compliant, C = compliant.

TABLE 5

Efficacy of antimicrobial storage of different batches with 0.3% of xanthan gum and with different amounts of propylene glycol.

| | Percentage composition (in % w/w) | | |
|---|---|---|---|
| Ingredients | CE5 | C (35% PG) | D (45% PG) |
| Torasemide | 0.20 | 0.20 | 0.20 |
| Tromethamine | 1.50 | 1.50 | 1.50 |
| Xanthan gum | 0.30 | 0.30 | 0.30 |
| Propylene glycol | 0.00 | 35.00 | 45.00 |
| Purified water q.s. w/w | 98.00 | 63.00 | 53.00 |
| Total (% w/w) | 100.00 | 100.00 | 100.00 |
| Efficacy of antimicrobial storage (Ph Eur) | NC | C | C |
| S. aureus | NC | C | C |
| E. coli | C | C | C |
| Ps. aeruginosa | NC | C | C |
| C. albicans | NC | C | C |
| A. brasiliensis | NC | C | C |
| Efficacy of antimicrobial storage (USP) | NC | C | C |
| S. aureus | C | C | C |
| E. coli | C | C | C |
| Ps. aeruginosa | NC | C | C |
| C. albicans | C | C | C |
| A. brasiliensis | C | C | C |

NC = not compliant, C = compliant.

TABLE 6

Evaluation of the antimicrobial efficacy of propylene glycol as a function of its content with 0.15% of Carbopol 971P. They differ from one another in the content of propylene glycol: 0, 30, 45 and 60% w/w.

| | Percentage composition (in % w/w) | | | |
|---|---|---|---|---|
| Ingredients | CE6 | E | F | G |
| Torasemide | 0.20 | 0.20 | 0.20 | 0.20 |
| Tromethamine | 1.50 | 1.50 | 1.50 | 1.50 |
| Propylene glycol | / | 30.00 | 45.00 | 60.00 |
| Carbopol 971P | 0.15 | 0.15 | 0.15 | 0.15 |
| Purified water q.s. w/w | q.s. 100.00 | q.s. 100.00 | q.s. 100.00 | q.s. 100.00 |
| Efficacy of antimicrobial storage (PhEur) | NC | C | C | C |
| S. aureus | C | C | C | C |
| E. coli | C | C | C | C |
| Ps. aeruginosa | C | C | C | C |
| C. albicans | C | C | C | C |
| A. brasiliensis | NC | C | C | C |

NC = not compliant, C = compliant.

TABLE 7

Evaluation of the antimicrobial efficacy of propylene glycol as a function of its content with 0.15% of xanthan gum. They differ from one another in the content of propylene glycol: 0, 45 and 60% w/w.

| | Percentage composition (in % w/w) | | |
|---|---|---|---|
| Ingredients | CE7 | H | I |
| Torasemide | 0.20 | 0.20 | 0.20 |
| Tromethamine | 1.50 | 1.50 | 1.50 |
| Propylene glycol | / | 45.00 | 60.00 |
| Xanthan gum | 0.20 | 0.20 | 0.20 |
| Purified water q.s. w/w | q.s. 100.00 | q.s. 100.00 | q.s. 100.00 |
| Efficacy of antimicrobial storage (Ph Eur) | NC | C | C |
| S. aureus | NC | C | C |
| E. coli | C | C | C |
| Ps. aeruginosa | NC | C | C |
| C. albicans | NC | C | C |
| A. brasiliensis | NC | C | C |

NC = not compliant, C = compliant.

The compositions including a content grey ha or equal to 30% of propylene glycol gave an antimicrobial preservation efficacy meeting the European Pharmacopeia, the pharmacopeia having the strictest criteria (narrower ranges of tolerance) terms of antimicrobial preservation efficacy, in contrast to the compositions including less than 30% of organic solvent (i.e. propylene glycol).

Example 4

Comparison of Stability of Compositions Including Furosemide or Torasemide

Compositions CE-A to CE-F are prepared according to the following procedure:

1) add ethanol to propylene glycol and homogenize;
2) add citrate buffer to the mixture obtained in step 1;
3) add the active ingredient (furosemide or torasemide) to the mixture obtained in step 2;
4) add HPC (hydroxypropylcellulose) to the mixture obtained in step 3.

Compositions CE-A to CE-F all have a pH between 6.0 and 6.6.

TABLE 7

Composition and appearance of compositions CE-A to CE-F.

| Formula | CE-A (% w/w) | CE-B (% w/w) | CE-C (% w/w) | CE-D (% w/w) | CE-E (% w/w) | CE-F (% w/w) |
|---|---|---|---|---|---|---|
| Furosemide | 0.125 | | | | | |
| Torasemide | | 0.200 | 0.200 | 1.000 | 3.000 | 3.000 |
| Propylene glycol | 48.438 | 48.363 | 60.000 | 48.363 | 24.313 | 48.363 |
| Absolute ethanol | 38.750 | 20.000 | 20.000 | 38.750 | 60.000 | 38.750 |
| HPC | 3.000 | 3.000 | 3.000 | 3.000 | 3.000 | 3.000 |
| Citrate buffer | 9.688 | 28.438 | 16.800 | 8.888 | 9.688 | 6.888 |
| TOTAL | 100.001 | 100.000 | 100.000 | 100.001 | 100.001 | 100.001 |
| Appearance | L | S | P | S | S | S |

L = clear solution, S = suspension, P = particles.

These results show that furosemide and torasemide are not simply interchangeable.

The invention claimed is:

1. An aqueous composition comprising:
   torasemide;
   a buffer or an alkalizing agent; and
   an organic solvent that is an alcohol derived from propane, wherein a concentration of the organic solvent by weight is greater than or equal to 30% relative to a total weight of the aqueous composition, wherein the aqueous composition is physically, chemically, and antimicrobially stable for at least 24 months when stored at a temperature between 25 and 30° C.

2. The aqueous composition according to claim 1, wherein a concentration of the torasemide by weight is between 0.01% and 5% relative to the total weight of the composition.

3. The aqueous composition according to claim 1, wherein the buffer or alkalizing agent is selected from the group consisting of tromethamine (TRIS), triethanolamine, diethanolamine, monoethanolamine, sodium hydroxide, potassium hydroxide, ammonium hydroxide and meglumine, wherein a concentration of the buffer or of the alkalizing agent by weight is between 1 and 5% relative to the total weight of the aqueous composition.

4. The aqueous composition according to claim 1, further comprising a rheology modifier, selected from the group consisting of synthetic hydrophilic polymers of acrylic acid, polysaccharides, gums, polyvinyl povidone, poloxamers, hydrophilic silica and poly(meth)acrylates, wherein a concentration of rheology modifier by weight is between 0.01 and 10% relative to the total weight of the aqueous composition.

5. The aqueous composition according to claim 1, further comprising a sweetener.

6. The aqueous composition according to claim 1, wherein a viscosity of the aqueous composition is between 0.001 and 5 Pa·s.

7. The aqueous composition according to claim 1, further comprising a pharmaceutically acceptable excipient.

8. The aqueous composition according to claim 1, wherein a pH of the aqueous composition is between 7.5 and 10.

9. A method of treatment, comprising:
   determining the existence of clinical signs associated with congestive heart failure, treatment of kidney diseases and hypertension are present in a subject; and
   applying a composition to the subject based on the determining, wherein the composition comprises:
   torasemide;
   a buffer or an alkalizing agent; and
   an organic solvent that is an alcohol derived from propane, wherein a concentration of the organic solvent by weight is greater than or equal to 30% relative to a total weight of the composition, wherein only the torasemide is an active ingredient of the composition that treats the congestive heart failure, treatment of kidney diseases and/or hypertension present in the subject.

10. A method of manufacturing a composition, the method comprising:
    providing an aqueous composition comprising torasemide; and
    applying an organic solvent to the aqueous composition, wherein the organic solvent is an alcohol derived from propane, at a concentration by weight greater than or equal to 30%, wherein a composition defined by the aqueous composition and the organic solvent applied to the aqueous composition is physically, chemically, and antimicrobially stable for at least 24 months when stored at a temperature between 25 and 30° C.

11. A method for preparing a composition, comprising:
    (a) adding a buffer or an alkalizing agent to water at room temperature and stirring to obtain mixture 1,
    (b) adding torasemide to mixture 1 and stirring to obtain mixture 2,
    (c) gradually adding a rheology modifier, with stirring, to obtain mixture 3,
    (d) stirring until a clear solution is obtained, to obtain mixture 4,
    (e) adding an organic solvent that is an alcohol derived from propane, wherein a concentration of the organic solvent by weight is greater than or equal to 30% relative to a total weight of the composition and stirring until a clear solution is obtained, to obtain mixture 5, wherein mixture 5 is physically, chemically, and antimicrobially stable for at least 24 months when stored at a temperature between 25 and 30° C.

12. A containment system comprising:
a container; and
a composition comprising:
  torasemide;
  a buffer or an alkalizing agent; and
  an organic solvent that is an alcohol derived from propane, wherein a concentration of the organic solvent by weight is greater than or equal to 30% relative to a total weight of the composition, wherein the composition is physically, chemically, and antimicrobially stable for at least 24 months when stored at a temperature between 25 and 30° C.;
wherein the composition is present within the container.

13. A kit-comprising:
a containment system comprising:
  a container; and
  a composition comprising:
    torasemide;
    a buffer or an alkalizing agent; and
    an organic solvent that is an alcohol derived from propane, wherein a concentration of the organic solvent by weight is greater than or equal to 30% relative to a total weight of the composition, wherein the composition is physically, chemically, and antimicrobially stable for at least 24 months when stored at a temperature between 25 and 30° C.;
wherein the composition is present within the container; and
a system for administering the composition.

14. The aqueous composition according to claim 1, wherein the alcohol is selected from the group consisting of propylene glycol, glycerol, propane-1,3-diol, propanol, isopropanol and mixtures thereof.

15. The method of treatment according to claim 9, wherein the alcohol is selected from the group consisting of propylene glycol, glycerol, propane-1,3-diol, propanol, isopropanol and mixtures thereof.

16. The method of treatment according to claim 9, wherein the subject is a human.

17. The method of treatment according to claim 9, wherein the subject is an animal.

18. The method according to claim 10, wherein the organic solvent endows the aqueous composition with antimicrobial properties.

19. The method according to claim 10, wherein the alcohol is selected from the group consisting of propylene glycol, glycerol, propane-1,3-diol, propanol, isopropanol and mixtures thereof.

20. The method according to claim 11, wherein the alcohol is selected from the group consisting of propylene glycol, glycerol, propane-1,3-diol, propanol, isopropanol and mixtures thereof.

21. The method according to claim 11, wherein the method is performed under an inert atmosphere.

22. The method according to claim 11, wherein process (d) comprises adding a pharmaceutically acceptable excipient.

23. The method according to claim 11, further comprising adjusting the volume, with stirring.

24. The method according to claim 11, further comprising adjusting the pH.

25. The containment system according to claim 12, wherein the alcohol is selected from the group consisting of propylene glycol, glycerol, propane-1,3-diol, propanol, isopropanol and mixtures thereof.

26. The containment system according to claim 12, wherein the container is a bottle.

27. The kit according to claim 13, wherein the alcohol is selected from the group consisting of propylene glycol, glycerol, propane-1,3-diol, propanol, isopropanol and mixtures thereof.

28. The kit according to claim 13, wherein the container is a bottle.

29. The aqueous composition according to claim 1, wherein only the torasemide is an active ingredient of that composition that treats congestive heart failure, treatment of kidney diseases and/or hypertension present in a subject.

30. The method of treatment according to claim 9, wherein the composition is physically, chemically, and antimicrobially stable for at least 24 months when stored at a temperature between 25 and 30° C.

31. The method of treatment according to claim 30, wherein a pH of the composition is between 7.5 and 10.

32. The method of manufacture according to claim 10, wherein only the torasemide is an active ingredient of that composition that treats congestive heart failure, treatment of kidney diseases and/or hypertension present in a subject.

33. The method of manufacture according to claim 10, wherein a pH of the composition is between 7.5 and 10.

34. The method of preparing a composition according to claim 11, wherein only the torasemide is an active ingredient of mixture 5 that treats congestive heart failure, treatment of kidney diseases and/or hypertension present in a subject.

35. The method of preparing a composition according to claim 11, wherein a pH of mixture 5 is between 7.5 and 10.

36. The containment system according to claim 12, wherein only the torasemide is an active ingredient of that composition that treats congestive heart failure, treatment of kidney diseases and/or hypertension present in a subject.

37. The containment system according to claim 12, wherein a pH of the composition is between 7.5 and 10.

38. The kit according to claim 13, wherein only the torasemide is an active ingredient of that composition that treats congestive heart failure, treatment of kidney diseases and/or hypertension present in a subject.

39. The kit according to claim 13, wherein a pH of the composition is between 7.5 and 10.

* * * * *